(12) United States Patent
Müller

(10) Patent No.: US 7,390,500 B2
(45) Date of Patent: Jun. 24, 2008

(54) TRANSDERMAL THERAPEUTIC SYSTEM (TTS) WITH FENTANYL AS A ACTIVE INGREDIENT

(75) Inventor: Walter Müller, Andernach (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 655 days.

(21) Appl. No.: 10/487,375

(22) PCT Filed: Jul. 10, 2002

(86) PCT No.: PCT/EP02/07663

§ 371 (c)(1), (2), (4) Date: Feb. 20, 2004

(87) PCT Pub. No.: WO03/018071

PCT Pub. Date: Mar. 6, 2003

(65) Prior Publication Data

US 2004/0234583 A1 Nov. 25, 2004

(30) Foreign Application Priority Data

Aug. 24, 2001 (DE) ................. 101 41 651

(51) Int. Cl.
*A61F 13/00* (2006.01)
(52) U.S. Cl. .................................... 424/449
(58) Field of Classification Search ............ 424/448, 424/449, 447
See application file for complete search history.

(56) References Cited

U.S. PATENT DOCUMENTS

| 4,588,580 A | 5/1986 | Gale et al. | |
|---|---|---|---|
| 4,645,502 A * | 2/1987 | Gale et al. | 424/448 |
| 5,120,546 A * | 6/1992 | Hansen et al. | 424/449 |
| 5,230,898 A * | 7/1993 | Horstmann et al. | 424/449 |
| 5,310,559 A * | 5/1994 | Shah et al. | 424/448 |
| 6,110,488 A * | 8/2000 | Hoffmann | 424/449 |
| 6,221,383 B1 | 4/2001 | Miranda et al. | |
| 6,893,655 B2 * | 5/2005 | Flanigan et al. | 424/448 |

FOREIGN PATENT DOCUMENTS

| DE | 19958 554 A1 | 1/2001 |
|---|---|---|
| WO | WO 89/10108 | 11/1989 |
| WO | WO 95/18603 | 7/1995 |
| WO | WO 99/56782 | 11/1999 |
| WO | WO 01/01967 A1 | 1/2001 |

OTHER PUBLICATIONS

Grond et al., "Clinical Pharmacokinetics of Transdermal Opioids", Drug Delivery Systems, Clin. Pharmacokinet., vol. 38, No. 1, pp. 59-89, Jan. 2000.

Osborne et al., "Skin Penetration Enhancers Cited in the Technical Literature", http://www.pharmtech.com/technical/osborne/osborne.htm, Jun. 5, 1999.

* cited by examiner

*Primary Examiner*—Sharon E. Kennedy
(74) *Attorney, Agent, or Firm*—Frommer Lawrence & Haug LLP

(57) ABSTRACT

The invention relates to a transdermal therapeutic systems with fentanyl or an analogous fentanyl derivative as active ingredient. In order to prevent inadvertent overdosage by uncontrolled release of active ingredient as a result of damage, the active ingredient is contained in fluid-filled microreservoirs in the layer containing the active ingredient. The layer containing the active ingredient can optionally be provided with a membrane.

22 Claims, 3 Drawing Sheets

TRANSDERMAL THERAPEUTIC SYSTEM (TTS) WITH FENTANYL AS A ACTIVE INGREDIENT

FIELD OF THE INVENTION

The present invention relates to a transdermal therapeutic system (TTS) containing the active substance fentanyl.

BACKGROUND OF THE INVENTION

Fentanyl and fentanyl analog derivatives such as sulfentanyl, carfentanyl, lofentanyl, and alfentanyl are extremely active analgesics. Their low dosage and their physicochemical properties such as, for example, the n-octanol/water partition coefficient, the melting point, and the molecular weight make it possible to supply the substances transdermally in an effective amount, and their pharmacokinetic properties such as the rapid metabolization and the relatively narrow therapeutic index make their transdermal supply desirable.

Indeed, for a number of years a fentanyl TTS has been on the market. This system is of the type known as a reservoir system. A reservoir system is a TTS which contains the active substance in a liquid or gel formulation in a pouch formed from an impermeable film and a membrane which is permeable for the active substance. The impermeable film acts as a backing layer, in order to prevent the liquid or gel formulation of the active substance emerging on the side of the pouch facing away from the skin. The membrane serves to regulate the rate of active substance release from the skin-facing side of the pouch. On this side, the membrane additionally possesses an adhesive layer for attaching the overall TTS to the skin.

In this specific case (Durogesic® TTS), fentanyl is in solution in a mixture of ethanol and water. Further details of this system can be found in U.S. Pat. No. 4,588,580 or DE 35 26 339, both of which contain a detailed description.

However, reservoir systems have a major disadvantage, namely that in the event of a leak (e.g., a simple mechanically induced damage, a cut or tear, splitting of the weld seam, etc.) in the pouch containing the active substance formulation, the active substance may come into contact with the skin over a large area and, as a consequence of this contact, may be absorbed in, excessive doses. Especially in the case of fentanyl and the fentanyl analog derivatives, this is potentially fatal, since overdose leads very rapidly to respiratory depression and hence fatal incidents. A number of such fatal or near-fatal incidents have been described in *Clinical Pharmacokint..* 2000, 38 (1), 59-89.

SUMMARY OF THE INVENTION

It is an object of the present invention to provide a transdermal therapeutic system comprising the active substance fentanyl and/or fentanyl analog derivatives which offers the user increased security against inadvertent overdose.

DETAILED DESCRIPTION OF THE INVENTION

This object is achieved by means of a transdermal therapeutic system which comprises a backing layer, an active substance layer, and a protective layer, to be removed before use. The active substance layer is composed of a polymer into which a multiplicity of liquid microreservoirs have been incorporated. These microreservoirs contain the active substance.

As has been found, despite the fact that the active substance is contained in a liquid formulation within the active substance layer, said layer is absolutely leakproof even when damaged mechanically (cuts, tears, abrasion, etc.). The user is therefore at no risk in respect of uncontrolled release or inadvertent overdose as a consequence of unintended or deliberate damage to the active substance layer.

From a purely external standpoint, there is no difference between this kind of transdermnal therapeutic system and the second major TTS type, a matrix system. With the TTS of the invention, the internal structure of the active substance layer can be perceived only under the microscope. The liquid microreservoirs are embedded in the form of small droplets in the (preferably self-adhesive) active substance layer. (These droplets adopt an approximately spherical form.) A transdermal therapeutic system with an active substance layer constructed in this way will be referred to hereinbelow as a "microreservoir system".

These liquid microreservoirs have an average diameter of about 5-50 μm. In any case, however, they must be smaller than the thickness of the active substance layer, since otherwise the active substance liquid could escape. The size of the microreservoirs can be influenced by the choice of suitable liquids and by regulating certain parameters during the preparation process.

Figure 1:
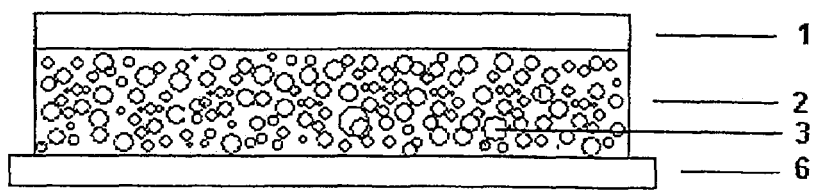
FIG. 1 illustrates the microreservoir system.

Like a matrix system, the microreservoir system of the invention is thus composed at its most simple of three layers: a backing layer, impermeable to the active substance; the self-adhesive active substance layer, with the microreservoirs; and a protective layer, to be removed before use. A system of this kind is illustrated in FIG. 1.

Figure 2:
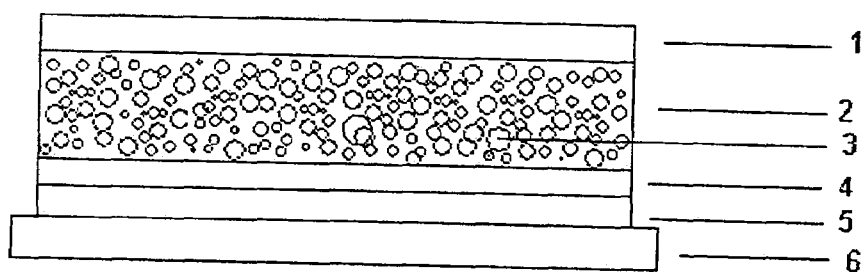
FIG. 2 illustrates the microreservoir system with membrane.

Even in the case of a microreservoir system, however, it may be necessary in certain circumstances to limit the amount of active substance to be delivered by the transdermal therapeutic system over a certain period of time. This can be achieved by means of a membrane which adjoins the active substance layer on the skin side, and which for attachment to the skin may additionally be provided with an adhesive layer. During the preparation process, this skin-side adhesive layer may be provided with a limited amount of active substance which, following application of such a microreservoir system, is delivered to the skin and hence into the organism in a way which cannot be controlled by the membrane. The purpose of this measure is to shorten the time until a therapeutic plasma level is reached (known as the "lag time"). A microreservoir system with membrane is depicted in FIG. 2.

Suitable active substances include fentanyl and/or fentanyl analog derivatives, preferably sulfentanyl, carfentanyl, lofentanyl, and alfentanyl. The active substance is preferably in the form of the free base; alternatively, it may be used in the form of a pharmaceutically acceptable salt or as a mixture of the free base with a pharmaceutically acceptable salt of said base. Examples of suitable salts include the hydrochlorides, hydrobromides, sulfates, hydrogen sulfates, citrates, and tartrates.

As already mentioned, fentanyl and the fentanyl analog derivatives possess a narrow therapeutic index. This means that the active substance release rate of a transdermal therapeutic system containing fentanyl or a fentanyl analog must be controlled with very great precision.

It has been found that the polymer or polymer blend which provides the active substance layer with its internal cohesion, and in which the microreservoirs are embedded, must meet certain requirements regarding dissolution capacity for the active substance and miscibility with the liquids which form the microreservoirs. Accordingly, the dissolution capacity for the active substance should be low, so that the majority of the active substance is located within the microreservoirs and not in the polymer itself. Further, the polymer should be substantially immiscible with the liquids which form the microreservoirs. These measures ensure that, first, the formation of microreservoirs is actually possible and that, secondly, the dissolution capacity of the polymer phase for the active substance is not too high.

Polymers which have been found to be suitable include hydrophobic polymers, which preferably possess pressure sensitive adhesion. These include polyisobutylenes and silicones (polysiloxanes). Amine-resistant polysiloxanes have proven particularly suitable. In solubility studies it has been found that the solubility of the active substance in such polymers is low. For example, fentanyl in base form has a solubility in such polymers of less than 0.5% by weight.

Amine-resistant polymers of this kind are produced, for example, by Dow Corning and are sold under the trade name BIO-PSA. The tackiness of these polymers ranges from non-tacky via moderately strongly to strongly tacky, the appropriate tack also being adjustable by blending of the individual types and/or by adding low molecular mass substances such as silicone oil, for example.

The advantage of the amine-resistant polysiloxanes is that they possess no free siloxanol groups and therefore do not tend to undergo condensation reactions in the presence of basic active substances or salts of basic active substances, with adverse consequences for the bond strength. Moreover, the interaction with the polar groups of the active substance molecules is lessened.

Solvents which can be used for the polymer include low-polarity and/or hydrophobic solvents. Amine-resistant polysiloxanes are offered in a variety of solvent systems. The most suitable solvents for the production of transdermal therapeutic systems in the context of this invention are n-heptane and comparable hydrocarbons, since the liquids envisaged for the microreservoirs are of only poor miscibility with this solvent.

As a result, during preparation, the solution of the active substance in the micro-reservoir liquid can be dispersed in the solution of the polysiloxane and thus the size of the microreservoirs in the composition to be coated can be set at this stage by virtue of the stirring conditions. For the purposes of the present description, a dispersion is a system which is composed of a continuous phase (which is made of polymer) and of the microreservoirs, which are not mutually contiguous (and which are made up of the liquid droplets).

The liquid, which constitutes an important ingredient of the microreservoirs, should be at least partly miscible both with water and with organic solvents. It may therefore also be referred to as ambiphilic.

Moreover, the liquid should possess a good solvency for the active substance, in order to accommodate the required amount of active substance in customary TTS active substance layer thicknesses of about 30 to 300 µm, correspond to a coating weight of 30-300 g/m².

Dipropylene glycol, diethylene glycol monoethyl ether, diethylene glycol diethyl ether, diethylene glycol monomethyl ether, diethylene glycol dimethyl ether, 1,3-butanediol, 2,2-dimethyl-4-hydroxymethyl-1,3-dioxolane, 2-pyrrolidone, and N-methylpyrrolidone have proven particularly suitable. Instead of the substances alone it is of course also possible to take blends thereof.

The saturation solubilities of fentanyl, measured in different liquids suitable for use as the microreservoirs, are shown in table 1.

TABLE 1

Saturation solubility of fentanyl in different liquids

| Microreservoir liquid | Solubility [% w/w] |
|---|---|
| 1,3-Butanediol | 10 |
| Dipropylene glycol | 18 |
| Transcutol* | 25 |
| Diethylene glycol diethyl ether | 26 |
| N-Methylpyrrolidone | 26 |

*Diethylene glycol monoethyl ether

Accordingly, the solubility of fentanyl in base form is higher by a factor of about is 20-50 in the liquids envisaged for the microreservoirs than in the polysiloxane polymer. This is more than sufficient to accommodate the required amount of active substance within a microreservoir matrix not exceeding 200 µm in thickness, in a system with an acceptable areal size.

The high solubility of fentanyl in the liquids envisaged for the microreservoirs coupled with its low solubility in the silicone polymer has the effect, moreover, that by far the predominant portion of the fentanyl is actually located within the microreservoirs and not in solution in the polymer phase.

Prior to application of a TTS of the invention, preferably more than 50% of the total active substance present in the TTS is situated within the microreservoirs, since otherwise, because of the poor solubility in the polymer, the active substance layers are too thick and the service properties poor for the finished system.

The total concentration of the active substance in the active substance layer is only between 2 and 5% by weight, which then also corresponds approximately to the saturation concentration of the active substance in the polymer. This means that, despite the low concentration, the thermodynamic activity of the active substance is at a maximum, i.e., at or just below 1.

The fraction of the microreservoirs in the active substance layer may amount to up to 40% by weight, although it is advantageous not to exceed 30% by weight.

It has proven advantageous to add to these liquids a substance which raises their viscosity. Such substances may comprise polymers which are capable of forming a gel with the liquid. Mention may be made by way of example of ethylcellulose and hydroxypropylcellulose, which are also used in the examples. This measure facilitates the dispersibility of the liquid in the solution of the polymer and may also result in smaller microreservoir diameters.

For microreservoir systems of the invention which are provided with a membrane, either microporous membranes or what are known as distribution membranes may be used. Microporous membranes are films provided with microscopic pores or channels. Here, the transport of active substance is substantially through these pores or channels, which must therefore be filled with a medium which is diffusible for the active substance (e.g., a liquid, gas, gel or other material). The number, the internal surface area, and the size of the pores, and the physicochemical properties of the pore or channel filling substantially determine the release of active substance (permeation rate).

Distribution membranes do not possess any pores; in other words, the active substance must diffuse through the membrane material itself. When membranes of this kind are used, it is the thickness of the membrane, and the solubility and diffusion coefficient of the active substance in the membrane material, which determine the release of active substance. Distribution membranes which have proven particularly highly suitable are those based on copolymers of ethylene and vinyl acetate (EVA). Membranes of this kind are available in a variety of thicknesses and with different compositions. Customary thicknesses range between 20 and 150 µm, and the vinyl acetate (VA) content between 2 and 25% by weight.

Since the VA content has an effect on the solubility and the diffusion coefficient of the active substances in the EVA polymers, it is a further important membrane characterization parameter where membranes made of this material are being used. In the examples, a membrane 50 µm thick with a VA content of 9% by weight has been used. The permeation rates achieved using this membrane can be raised through the use of thinner membranes or membranes having a higher VA content. Naturally, the use of thicker membranes and the reduction of the VA content has the opposite effect.

Especially when systems without membrane control are used, the active substance intake, i.e., the amount of active substance delivered by the TTS that is actually absorbed via the skin into the blood circulation is also dependent on the permeability of the skin. The outer skin layer in particular, the stratum corneum, forms the principal barrier against penetrative active substances. This barrier function can be lowered through the use of what are called enhancers, thereby increasing the active substance intake. Enhancers are known to the skilled worker, for example, from the publication "Skin penetration enhancers cited in the technical literature" by David W. Osborne and Jill J. Henke, ViroTex Corporation, which can be called up on the Internet at http://www.pharmtech.com/technical/osborne/osborne.htm and which in order to avoid repetition is intended in its entirety to form part of the disclosure content of this specification.

For the transdermal therapeutic systems of the present invention it is possible with particular advantage to use fatty acid, fatty acid ester, fatty alcohol or glycerol ester enhancers, especially when fentanyl is the active substance being used.

For the preparation of the active substance layer, the active substance is dissolved in the liquid which forms the microreservoirs, and this solution is dispersed in the solution of the polymer. The resulting dispersion is then used to coat an appropriate substrate—normally a polyester film with an abhesive coating—the solvent of the polymer is removed by drying. The drying conditions should be chosen such that only a small proportion if any of the microreservoir solvent is removed. It has been found that the liquid and the solvent are preferably selected such that the solvent possesses a boiling temperature which is at least about 30°, with particular preference at least 50°, below the boiling temperature of the liquid.

The dry matrix film is then laminated to the backing layer of the system—usually an active substance impermeable film with a thickness of about 15 -30 µm—and the individual transdermal therapeutic systems are then punched from the overall laminate obtained.

The production of corresponding microreservoir systems comprising membranes is somewhat more complicated, but in terms of the coating and laminating process is no different from the production of known systems with the same layer sequence. In the examples, the production of microreservoir systems with and without membranes is described in detail.

Using three transdermal therapeutic systems provided by this invention, i.e. microreservoir systems with and without membranes, permeation studies were conducted using human epidermis and Franz diffusion cells, which are known to the skilled worker. The composition and the results are summarized in tables 2 to 5, with the preparation process described in detail in the examples.

TABLE 2

Composition of the microreservoir systems without membranes

| | Composition [% w/w] | | |
|---|---|---|---|
| Formulation | A | B | C |
| Ingredients | | | |
| Fentanyl base | 2.0 | 3.6 | 5.0 |
| BIO-PSA 4301* | 80.0 | 80.0 | 80 |
| 1,3-Butanediol | 17.46 | | |
| Dipropylene glycol | | 16.07 | |
| Transcutol** | | | 14.4 |
| Hydroxypropyl-cellulose | 0.54 | 0.33 | |
| Ethylcellulose 100 NF | | | 0.6 |
| Coating weight [g/m$^2$] | 130 | 85 | 65 |
| Matrix thickness, approx. [µm] | 140 | 95 | 75 |

*Amine-resistant silicone adhesive with high bond strength
**Diethylene glycol monoethyl ether

TABLE 3

Results of the permeation study with formulations A, B and C

| | Cumulative permeated fentanyl base [µg/cm$^2$]* | | | | | Average release rate |
|---|---|---|---|---|---|---|
| Formulation | 4 h | 8 h | 24 h | 48 h | 72 h | (µg/cm$^2$ * h) |
| A | 1.2 | 9.5 | 84.4 | 194.0 | 275.0 | 3.82 |
| B | 1.12 | 8.87 | 75.80 | 191.00 | 283.00 | 3.93 |
| C | 16.20 | 45.20 | 131.00 | 212.00 | 262.00 | 3.64 |

*Averages of n = 3

TABLE 4

Composition of the systems with control membrane

| | Composition [% w/w] | | |
|---|---|---|---|
| Formulation | D | E | F |
| Ingredients | | | |
| Reservoir layer | | | |
| Fentanyl base | 2.0 | 3.6 | 5.0 |
| BIO-PSA 4301* | 80.0 | 80.0 | 80 |
| 1,3-Butanediol | 17.46 | | |
| Dipropylene glycol | | 16.07 | |
| Transcutol** | | | 14.4 |
| Hydroxypropyl-cellulose | 0.54 | 0.33 | |
| Ethylcellulose 100NF | | | 0.6 |
| Coating weight [g/m$^2$] | 130 | 85 | 65 |
| Control membrane | | EVA membrane 50 µm, 9% VA | |
| Skin contact layer | | | |
| BIO-PSA 4301* | 100 | 100 | 100 |
| Coating weight [g/m$^2$] | 35 | 35 | 35 |

*Amine-resistant silicone adhesive with high bond strength
**Diethylene glycol monoethyl ether

TABLE 5

Results of the permeation study with formulations D, E and F

| Formulation | Cumulative permeated fentanyl base [µg/cm²]* | | | | | Average release rate [µg/cm² * h] |
|---|---|---|---|---|---|---|
| | 4 h | 8 h | 24 h | 48 h | 72 h | |
| D | 1.4 | 4.9 | 26.2 | 64.0 | 99.8 | 1.39 |
| E | 2.7 | 8.1 | 37.0 | 85.0 | 129.0 | 1.79 |
| F | 0.8 | 4.7 | 45.3 | 114.0 | 166.0 | 2.31 |

*Averages of n = 3

Comparing the permeation results of the microreservoir systems with and without a membrane it can be seen that the amount of active substance permeated after 72 hours is much lower in the case of the membrane systems, despite the active substance layers having the same composition. This can be attributed to the controlling effect of the membrane, which limits the delivery of active substance to a maximum irrespective of the particular nature of the skin.

Figure 3:
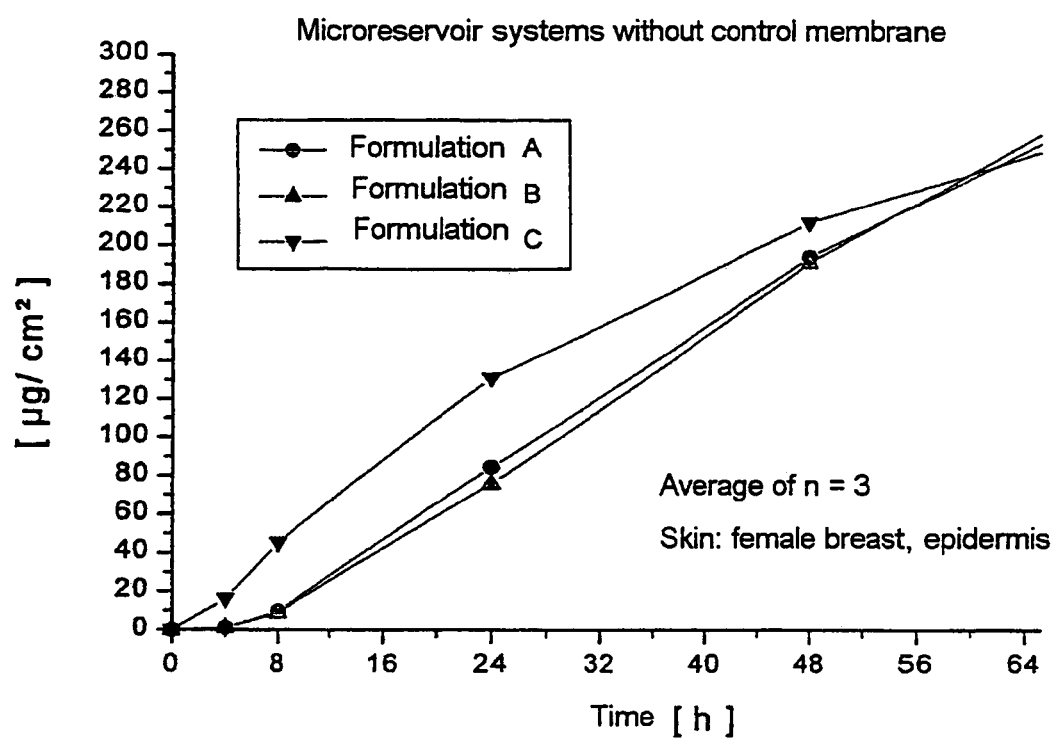
FIG. 3 illustrates the permeation profile of the microreservoir system of FIG. 1.
Figure 4:
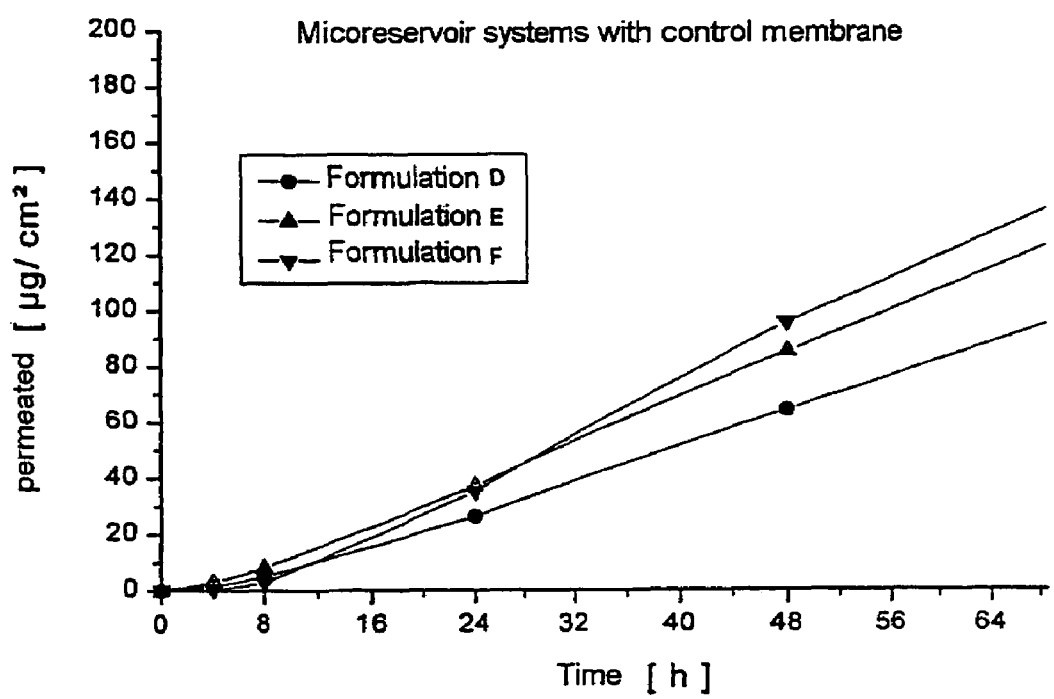
FIG. 4 illustrates the permeation profile of the microreservoir system of FIG. 2.

The graphs (FIGS. 3 and 4) also reveal that, as the result of the use of a membrane, the permeation profile is more linear and hence also the active substance intake in vivo is more uniform over the period of use. It is particularly evident in the case of formulation C, which shows the highest permeation rate.

The TTS present on the market (Durogesic®) is available in 4 strengths with average delivery rates of 25, 50, 75, and 100 µm/hour. With these figures and the results of the permeation studies, it is possible to calculate the surface areas of the systems with ease. The results are summarized in table 6.

TABLE 6

Calculated system surface areas of formulations A-F

| Delivery rate | Calculated area sizes (cm²) | | | | | |
|---|---|---|---|---|---|---|
| | A | B | C | D | E | F |
| 25 µm/h | 6.5 | 6.4 | 6.9 | 18.0 | 14.0 | 11.8 |
| 50 µm/h | 13.0 | 12.8 | 13.8 | 36.0 | 28.0 | 23.6 |
| 75 µm/h | 19.5 | 19.2 | 20.7 | 54.0 | 42.0 | 35.4 |
| 100 µm/h | 26.0 | 25.6 | 27.6 | 72.0 | 56.0 | 47.2 |

The calculated surface areas all lie within an acceptable range. The size of the microreservoir systems with membrane can be made smaller still through the use of thinner membranes or membranes with a higher VA content, although in that case the control of the delivery of active substance by the membrane will be less effective.

Microreservoir systems as provided by this invention therefore show very good permeation rates, which without a control membrane lead to TTS which are small in terms of area and are pleasant to wear. At the same time, there is absolutely no possibility of any risk to the patient from excessive active substance intake due to leakage.

In the case of microreservoir systems with membranes, the membrane control which limits the delivery of active substance results in patch sizes which are larger but still acceptable.

All in all, therefore, microreservoir systems for fentanyl and the fentanyl analog derivatives constitute a decisive step forward in terms of wear comfort and patient safety from the known prior art.

The preparation examples which follow describe the preparation of microreservoir systems with and without membranes.

EXAMPLE 1

Microreservoir System with 1,3-butanediol as Liquid, Formulation A 1 g of fentanyl base is dissolved in 9 g of 1,3-butanediol, thickened with 3% hydroxypropylcellulose. To this solution there are added 54.8 g of a 73% strength solution of an amine-resistant silicone adhesive in n-heptane (BIO-PSA 4301, Dow Corning) and the active substance solution is dispersed in the solution of the silicone adhesive by rapid stirring. The dispersion is then knife-coated onto an abhesively coated film, the protective layer to be removed later prior to use (Scotchpak 1022, 3M), in a thickness which following removal of the n-heptane by drying at 30° C. for 15 minutes results in a coating weight of 135 g/m². The dry film is then laminated with the active substance impermeable backing layer (Scotchpak 1220, 3M) and the finished transdermal therapeutic system is punched from the overall laminate which results.

EXAMPLE 2

Microreservoir System with Dipropylene Glycol as Liquid, Formulation B 1 g of fentanyl base is dissolved in 4.6 g of dipropylene glycol, thickened with 2% hydroxypropylcellulose. To this solution there are added 30.5 g of a 73% strength solution of an amine-resistant silicone adhesive in n-heptane (BIO-PSA 4301, Dow Corning) and the active substance solution is dispersed in the solution of the silicone adhesive by rapid stirring. The dispersion is then knife-coated onto an abhesively coated film, the protective layer to be removed later prior to use (Scotchpak 1022, 3M), in a thickness which following removal of the n-heptane by drying at 30° C. for 15 minutes results in a coating weight of 85 g/m². The dry film is then laminated with the active substance impermeable backing layer (Scotchpak 1220, 3M) and the finished transdermal therapeutic system is punched from the overall laminate which results.

EXAMPLE 3

Microreservoir System with Transcutol as Liquid, Formulation C 1 g of fentanyl base is dissolved in 3 g of Transcutol, thickened with 4% ethylcellulose. To this solution there are added 22 g of a 73% strength solution of an amine-resistant silicone adhesive in n-heptane (BIO-PSA 4301, Dow Corning), and the active substance solution is dispersed in the solution of the silicone adhesive by rapid stirring. The dispersion is then knife-coated onto an abhesively coated film, the protective layer to be removed later prior to use (Scotchpak 1022, 3M), in a thickness which following removal of the n-heptane by drying at 30° C. for 15 minutes results in a coating weight of 65 g/m². The dry film is then laminated with the active substance impermeable backing layer (Scotchpak 1220, 3M) and the finished transdermal therapeutic system is punched from the overall laminate which results.

EXAMPLES 4-6

Microreservoir Systems with Membranes, Formulations D, E, and F

The solution of an amine-resistant silicone adhesive (BIO-PSA 4301, Dow Corning) is knife-coated to an abhesively coated film (Scotchpak 1022, 3M) in a thickness such that removal of the n-heptane by drying at 30° C. for 15 minutes gives a coating weight of 20 g/m². The dried film is laminated with a membrane (EVA, 50 μm, 9% VA, 3M).

The protective layer is removed from the laminates from examples 1-3 and the laminate consisting of active substance layer and backing layer is laminated onto this membrane. The resulting overall laminate (formulations D, E and F) are then punched to give the finished transdermal therapeutic systems.

In the figures, the elements shown are as follows:
1=backing layer
2=active substance layer with microreservoirs
3=microreservoir
4=control membrane
5=skin contact layer
6=removable protective layer

The invention claimed is:

1. A transdermal therapeutic system (TTS) containing an active substance having increased security against overdose of the active substance comprising
   an active substance impermeable backing layer,
   an active substance layer, the active substance being fentanyl and/or a fentanyl analog derivative and/or a salt of fentanyl and/or a salt of a fentanyl analog derivative, where said active substance layer comprises a polymer or a polymer mixture with microreservoirs dispersed therein, wherein the active substance is dissolved in the microreservoirs and a membrane layer following the skin side comprised of an ethylene-vinyl acetate copolymer or a polyethylene or polypropylene microporous film;
   optionally a subsequent adhesive layer and
   a protective layer, which is removed before use.

2. The TTS of claim 1, characterized in that the polymer is a pressure sensitive adhesive polymer.

3. The TTS of claim 1, characterized in that the polymer is an amine-resistant polysiloxane.

4. The TTS of claim 1, characterized in that the microreservoirs contain a liquid.

5. The TTS of claim 1, wherein the microreservoirs have an average diameter of about 5 to 50 μm.

6. The TTS of claim 1, characterized in that at least 50% by weight of the active substance in the TTS is contained within the microreservoirs.

7. The TTS of claim 1, characterized in that the liquid comprises dipropylene glycol, diethylene glycol monoethyl ether, diethylene glycol diethyl ether, diethylene glycol monomethyl ether, diethylene glycol dimethyl ether, 1,3-butanediol, 2,2-dimethyl 4-hydroxymethyl-1,3-dioxolane, 2-pyrrolidone or N-methylpyrrolidone or a combination thereof.

8. The TTS of claim 1, characterized in that the liquid comprises an additive which increases the viscosity,.

9. The TTS of claim 1, characterized in that the concentration of the active substance in the active substance layer is below 5% by weight.

10. The TTS of claim 1, characterized in that the weight of the active substance layer per unit area is between 30 and 300 g/m².

11. The TTS of claim 1, characterized in that it comprises a membrane and where appropriate, an adhesive layer.

12. The TTS of claim 11, wherein where the membrane layer does not possess adhesive properties, an adhesive layer is located between membrane layer and protective layer.

13. The TTS of claim 12, characterized in that the ethylene-vinyl acetate copolymer has a vinyl acetate content of 2-25% and a thickness of between 20 and 150 μm.

14. The TTS of claim 1, characterized in that the active substance layer further comprises a substance which enhances the rate of permeation through human skin.

15. The TTS of claim 14, characterized in that the substance belongs to the group consisting of fatty acids, fatty acid esters, fatty alcohols, and glycerol esters.

16. The TTS of claim 8, wherein the additive which increases the viscosity is ethylcellulose or hydroxypropylcellulose.

17. The TTS of claim 9, characterized in that the concentration of the active substance in the active substance layer is below 4% by weight.

18. The TTS of claim 1, wherein the fraction of the microreservoirs in the active substance layer is up to 40% by weight.

19. The TTS of claim 1, wherein the polymer or polymer mixture is selected from the group consisting of polyisobutylenes.

20. The TTS of claim 11, wherein the membrane is 50 μm thick and is made of an ethylene-vinyl acetate copolymer having a vinyl acetate content of 9 wt.-%.

21. The TTS of claim 1, wherein the active substance being fentanyl or a salt of fentanyl, at least 50% by weight of the active substance in the TTS is contained within the microreservoirs, the liquid comprises dipropylene glycol, diethylene glycol monoethyl ether, diethylene glycol diethyl ether, diethylene glycol monomethyl ether, diethylene glycol dimethyl ether, 1,3-butanediol, 2,2-dimethyl4-hydroxymethyl-1,3-dioxolane, 2-pyrrolidone or N-methylpyrrolidone or a combination thereof, and the liquid comprises an additive which increases the viscosity.

22. The TTS of claim 21, wherein the active substance is present completely dissolved in the microreservoirs and the additive which increases the viscosity is ethylcellulose or hydroxypropylcellulose.

* * * * *